US00PP35498P2

(12) United States Plant Patent
Yamauchi et al.

(10) Patent No.: US PP35,498 P2
(45) Date of Patent: Nov. 21, 2023

(54) SHIITAKE MUSHROOM NAMED 'HS911'

(50) Latin Name: ***Lentinus edodes* (Berk) Sing**
Varietal Denomination: HS911

(71) Applicant: HOKKEN CO. LTD., Tochigi (JP)

(72) Inventors: Takahiro Yamauchi, Oyama (JP); Shin Takahashi, Tochigi (JP); Fumikazu Goto, Shimotsuke (JP)

(73) Assignee: HOKKEN CO. LTD., Shimotsuga-gun (JP)

( * ) Notice: Subject to any disclaimer, the term of this patent is extended or adjusted under 35 U.S.C. 154(b) by 0 days.

(21) Appl. No.: 17/803,988

(22) Filed: Feb. 22, 2023

(51) Int. Cl.
*A01H 5/00* (2018.01)
*A01H 15/00* (2006.01)

(52) U.S. Cl.
USPC ..... Plt./394
CPC ..... *A01H 15/00* (2013.01)

(58) Field of Classification Search
USPC ..... Plt./394
CPC ..... A01H 15/00
See application file for complete search history.

*Primary Examiner* — Keith O. Robinson
(74) *Attorney, Agent, or Firm* — Seckel IP, PLLC

(57) ABSTRACT

A new variety of shiitake mushroom 'HS911' that has a medium growth rate, medium to small-size scales, a slender stipe, and a very light dry weight at harvest maturity.

5 Drawing Sheets

Common name: Shiitake mushroom.
Botanical classification: *Lentinus edodes* (Berk) Sing.
Variety denomination: 'HS911'.

BACKGROUND OF THE NEW VARIETY

The present invention relates to a new and distinct variety of Shiitake mushroom, *Lentinus edodes* (Berk) Sing, which has been given the variety denomination 'HS911'.

This new mushroom has a medium growth rate, medium to small-size scales, a slender stipe, and a very light dry weight at harvest maturity.

ORIGIN OF THE VARIETY

The parent varieties are 'HS788' (mother) (not patented) and 'HL8516' (father) (not patented), respectively.

The mother variety 'HS788' was obtained as a new variety from parents 'Hokken 71go' (mother) (not patented) and 'HL0508' (father) (not patented). In March 2006, we selected for the superiority in mycelial elongation after a single spore isolation. Afterwards, we started log-cultivation characteristics tests in March 2011, physiological characteristic tests and genetic characteristic tests in July 2014, and obtained 'HS788' as a new variety.

The father variety 'HL8516' was obtained as a new variety from unknown parents. 'HL8516' is a control number assigned to a spore print obtained from a fruiting body collected in the wild.

In August 2015, we cross-bred 'HS788' with 'HL8516' and grew the new variety. The characteristics of the new variety were studied from March 2016 to July 2019. Afterwards, we started physiological characteristic tests and characteristic confirmation tests in August 2019, and the new variety was found to be stable in July 2020. We reproduced the variety asexually by vegetative reproduction using spawns for seedlings.

The variety was developed and propagated in Shimotsuga-gun, Tochigi, Japan.

Suitable times of sowing and harvesting are as follows:
Sowing: from early January to late December.
Harvesting: from early October to late May.

Cultivation of the variety does not require special conditions or treatments.

The variety is currently mainly intended for food production.

SUMMARY OF THE VARIETY

The variety is distinguished by a medium growth rate, medium to small-size scales, a slender stipe, and a very light dry weight at harvest maturity, especially as compared to the varieties 'Hokken 600 go' (not patented) and 'HS73' (not patented), which are otherwise relatively similar in cultivation.

A comparison with the varieties 'Hokken 600 go' and 'HS73' is as follows (average values):

TABLE 1

| | 'HS911' | 'Hokken 600 go' (not patented) | 'HS73' (not patented) |
|---|---|---|---|
| Growth rate at 25° C. | 4.55 mm/day (Medium to slow) | 5.12 mm/day (Medium) | 4.93 mm/day (Medium) |
| Size of scale: | 4.02 mm (Medium) | 3.12 mm (Medium to small) | 2.91 mm (Small) |
| Thickness of stipe | 20.41 mm (Thick) | 9.26 mm (Slender) | 13.43 mm (Medium) |
| Dry weight at harvest maturity | 5.90 g (Medium) | 2.61 g (Very light) | 4.10 g (Light) |

As compared to its parents 'HS788' and 'HL8516', the variety is distinguished by having its distribution of scales over the whole cap, as opposed to only over the periphery for 'HS788' (over the whole cap for 'HL8516'), by having its stipe shape in vertical section that is broader toward the cap, as opposed to broader toward the base for 'HS788' and cylindrical for 'HL8516', and by having crinkly gill shape, as opposed to straight for 'HL8516 (crinkly for 'HS788').

The comparison of the variety with its parents 'HS788' and 'HL8516' is summarized as follows:

TABLE 2

| | 'HS911' | 'HS788' (not patented) | 'HL8516' (not patented) |
|---|---|---|---|
| Cap: distribution of scales | Whole | Periphery | Whole |
| Stipe shape in vertical section | Broader toward cap | Broader toward base | Cylindrical |
| Gill shape | Crinkle | Crinkle | Straight |

BRIEF DESCRIPTION OF THE DRAWINGS

In the accompanying drawings, which are as nearly true as is reasonable possible to make in a color illustration of this type.

Figure 1A:
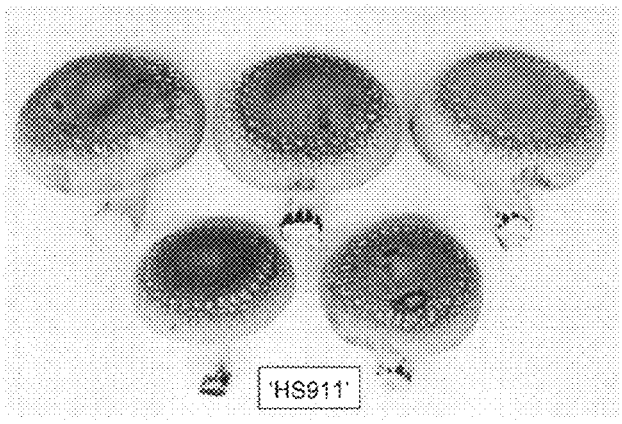
FIG. 1A is a color photograph showing a top surface of fruiting bodies of 'HS911'.
Figure 1B:
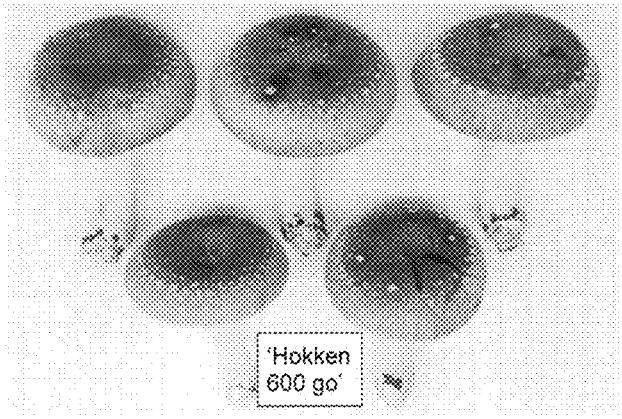
FIGS. 1B and 1C are color photographs showing a top surface of fruiting bodies of 'Hokken 600 go' and 'HS73' for comparison purposes.
Figure 1C:
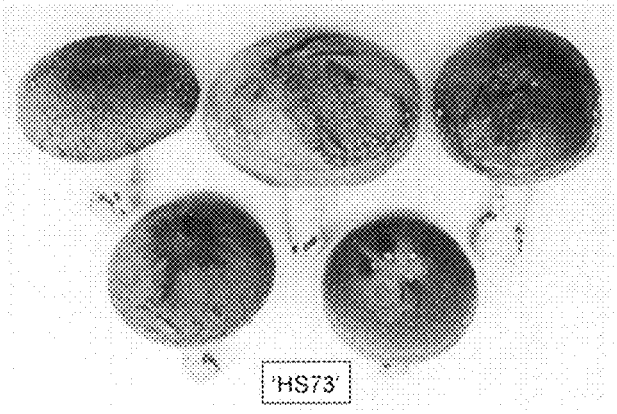
Figure 2A:
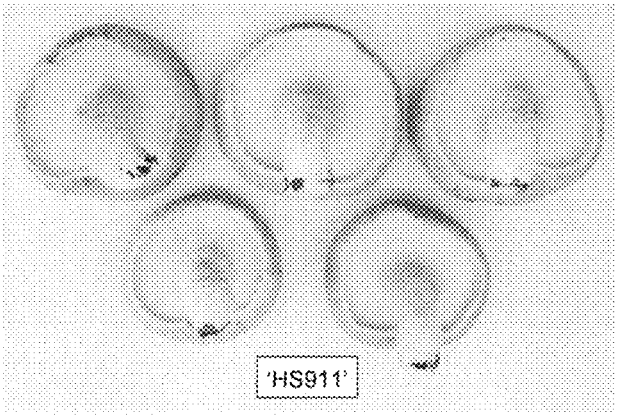
FIG. 2A is a color photograph showing a bottom surface and stem of fruiting bodies of 'HS911'.
Figure 2B:
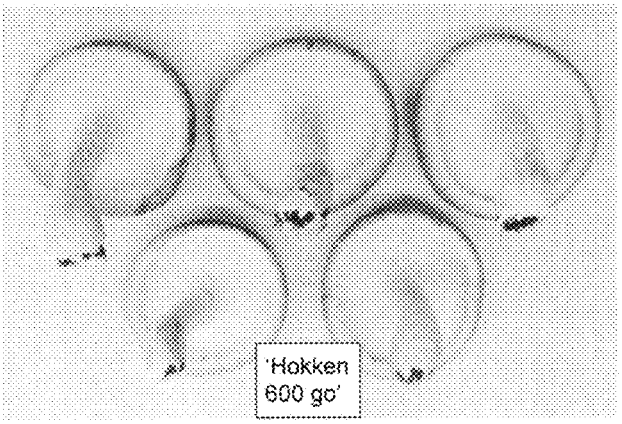
FIGS. 2B and 2C are color photographs showing a bottom surface of fruiting bodies of 'Hokken 600 go' and 'HS73' for comparison purposes.
Figure 2C:
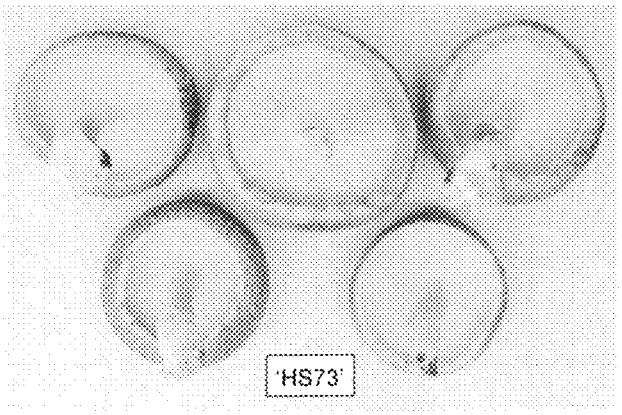
Figure 3A:
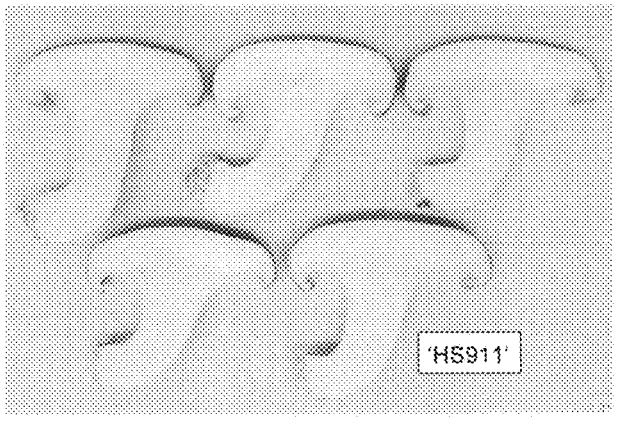
FIG. 3A is a color photograph showing a side view in cross-section of fruiting bodies of 'HS911'.
Figure 3B:
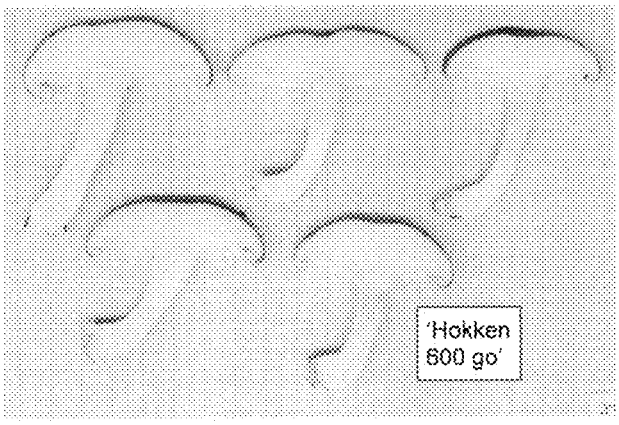
FIGS. 3B and 3C are color photographs showing a side view in cross-section of fruiting bodies of 'Hokken 600 go' and 'HS73' for comparison purposes.
Figure 3C:
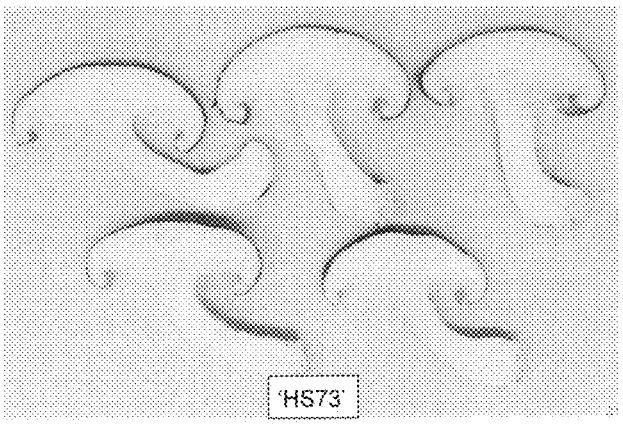
Figure 4A:
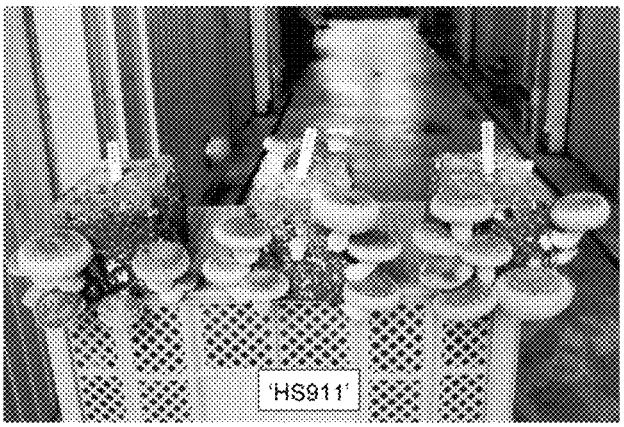
FIG. 4A is a color photograph showing fruiting bodies on culturing beds of 'HS911'.
Figure 4B:
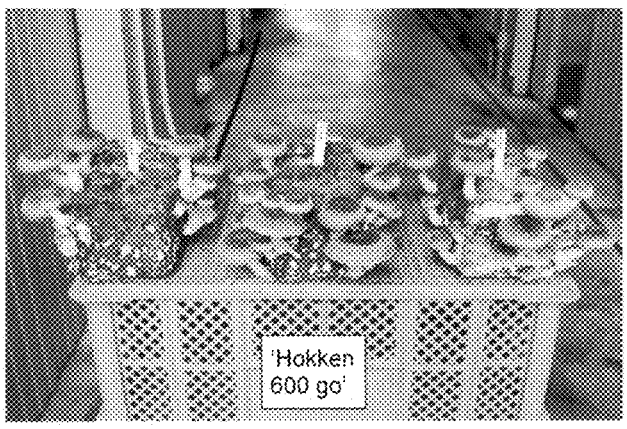
FIGS. 4B and 4C are color photographs showing fruiting bodies on culturing beds of 'Hokken 600 go' and 'HS73' for comparison purposes.
Figure 4C:
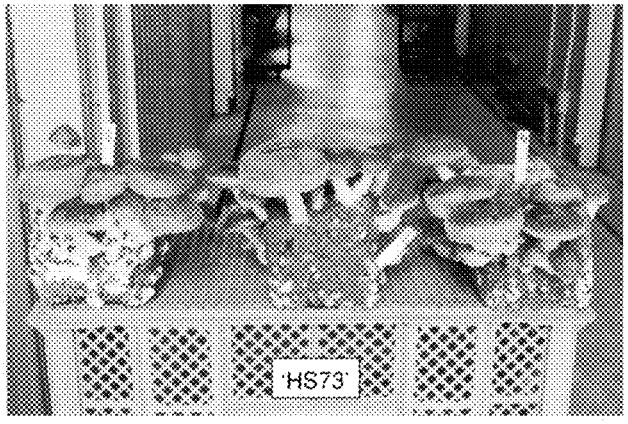
Figure 5A:
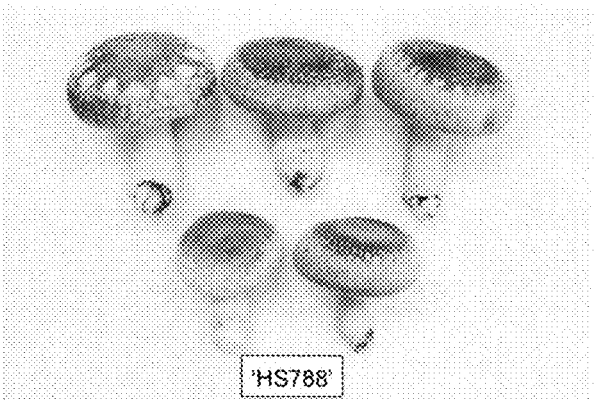
FIGS. 5A and 5B are color photographs showing a top surface, and a side view in cross-section, respectively, of fruiting bodies of parent 'HS788'.
Figure 5B:
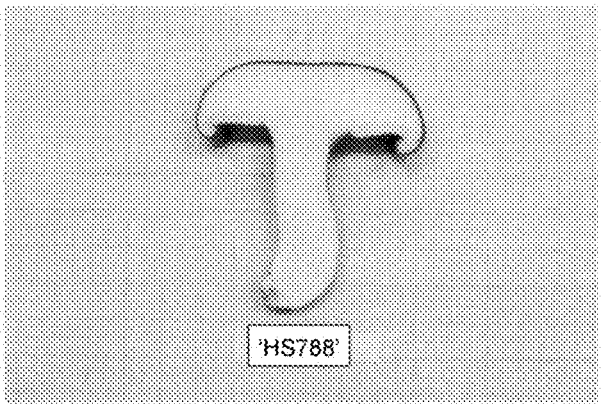
Figure 6A:
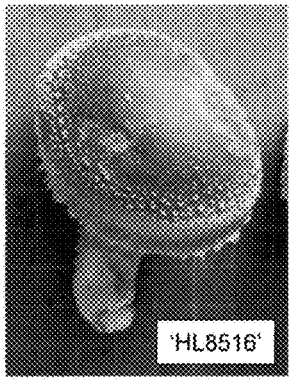
FIGS. 6A and 6B are color photographs showing a top surface, and a bottom surface, respectively, of fruiting bodies of parent 'HL8516'.
Figure 6B:
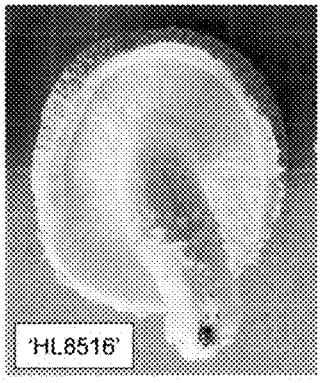

Due to chemical and/or digital development, processing and printing, the plants or portions of plants depicted in the photographs may or may not be precisely accurate, when compared to the actual botanical specimens.

DETAILED DESCRIPTION OF THE INVENTION

The botanical description and the photographs are of the 'HS911' plants at 146 days from sowing (and for the comparative plants: 'Hokken 600 go' at 110 days from sowing and 'HK73' at 117 days from sowing). Values as provided are averages.

The plants shown on the photographs were grown in Shimotsuga-gun, Tochigi, Japan.

Colors are given according to The R.H.S. Color Chart, Sixth Edition (2015).

BOTANICAL DESCRIPTION

Optimum temperature for mycelial growth: 26° C.
Temperature of mycelial growth:
- 10° *C.*—1.38 mm/day.
- 15° *C.*—2.68 mm/day.
- 20° *C.*—3.64 mm/day.
- 25° *C.*—4.55 mm/day.
- 30° *C.*—2.82 mm/day.

Shape of vertical cross-section (top): Round.
Diameter of cap: 85.60 mm.
Main color of apex: Moderate brown (RHS 200D).
Thickness of cap: 20.87 mm.
Firmness of cap: 0.81 N.
Arrangement of scales on cap: Periphery.
Size of scales: 4.02 mm.
Color of scales: Pale orange yellow (RHS 159B).
Gills in cap: Present (the gills are the hymenophore).
Shape of gills: Separate from stipe.
Arrangement of gills: Ripple.
Width of gills: 2.03 mm.
Color of gills: Pale orange yellow (RHS 159C).
Shape of stipe: Broader toward cap.
Length of stipe: 68.92 mm.
Thickness of stipe: 20.41 mm.
Color of stipe: Light yellowish pink (RHS 27A).
Firmness of stipe: 0.89 N.
Tinting of stipe: Present.
Presence of fluff: Present.
Period from inoculation to fruiting: 135 days.
Period from fruiting induction to harvest: 12 days.
Dry weight at maturity: 5.90 g.

We claim:

1. A new and distinct variety of shiitake mushroom named 'HS911', substantially as described and illustrated herein.

* * * * *